United States Patent
Nadol, Jr. et al.

(10) Patent No.: US 6,251,138 B1
(45) Date of Patent: Jun. 26, 2001

(54) HEARING PROSTHESIS

(75) Inventors: Joseph B. Nadol, Jr., Needham; Saumil N. Merchant, Acton, both of MA (US)

(73) Assignee: Massachusetts Eye & Ear Infirmary, Boston, MA (US)

(*) Notice: Subject to any disclaimer, the term of this patent is extended or adjusted under 35 U.S.C. 154(b) by 0 days.

(21) Appl. No.: 09/362,272

(22) Filed: Jul. 28, 1999

(51) Int. Cl.[7] .................................................. A61F 2/18
(52) U.S. Cl. ................................................................ 623/10
(58) Field of Search ............................ 623/10, 11.11, 623/23.64, 23.67

(56) References Cited

U.S. PATENT DOCUMENTS

| 4,297,748 | * | 11/1981 | Moloy ................................... 623/10 |
| 4,470,407 | * | 9/1984 | Hussein .................................. 128/6 |
| 5,356,430 | * | 10/1994 | Nadol, Jr. ............................... 623/10 |
| 5,480,433 | * | 1/1996 | Nadol, Jr. ............................... 623/10 |

* cited by examiner

Primary Examiner—David J. Isabella
(74) Attorney, Agent, or Firm—Fish & Richardson, PC

(57) ABSTRACT

This invention relates to surgical methods and prosthetic devices for ameliorating hearing loss in patients having ailments of the middle ear. The prosthetic device of the invention includes at least a synthetic gas-filled balloon having a pliant membrane of biocompatible material. The surgical method of the invention places the synthetic balloon in the patient's middle ear in contact with the tympanic membrane to restore tympanic membrane motion so as to enhance transfer of sound through the middle ear to the inner ear of the patient.

28 Claims, 4 Drawing Sheets

HEARING PROSTHESIS

BACKGROUND OF THE INVENTION

The present invention relates to surgical methods and prosthetic devices for ameliorating hearing loss in patients suffering from ailments of the middle ear.

Chronic otitis media (COM), a common inflammatory disease of the middle ear and mastoid, can affect 0.5 to 30% of the population (a conservative estimate of the number of people suffering from COM is over 5 million in the U.S. and over 120 million worldwide), and results in conductive hearing loss that can range in severity up to 60 dB. The main form of therapy for COM is surgical, i.e., mastoidectomy and tympanoplasty. Although tympanomastoid surgery is typically successful in controlling infection, a post-operative hearing loss of more than 20 dB persists in about 50% of patients. Such hearing loss is often significant, in the range of 40 to 60 dB. Non-aeration of the middle ear due to deposition of fibrous tissue or formation of fluid resulting from eustachian tube dysfunction is understood to be the main cause of such post-operative hearing loss.

Serous otitis media (OME) is another common disorder of the middle ear that can lead to conductive hearing loss ranging in severity up to 30–40 dB. A number of patients with OME fail to respond to medical therapy and hence require surgical intervention by way of a tympanostomy (ventilation) tube. In fact, tympanostomy tube placement is the most common operation performed in the United States, with over 1.3 million ears intubated annually. Such tubes, however, have several disadvantages that include the need for water precautions, and the potential for chronic perforations, focal tympanic membrane atrophy, formation of retraction pockets, cholesteatoma and tube extrusion.

The introduction of a small bubble of gas into the middle ear of patients with eustachian tube obstruction, in which the middle ear and mastoid are filled with serous fluid, improves the conductive hearing loss of such patients as long as the air bubble remains in the middle ear. This has led some investigators to inject air or other gases in the middle ear to improve hearing loss. Such gases, however, are short-lived in the middle ear due to absorption. Further, attempts to create long-lasting air pockets using silicone elastomers or an air-filled hollow body of silastic have failed to produce lasting benefit, presumably because of extrusion of the prosthesis and/or failure of the prosthesis to remain inflated.

U.S. Pat. No. 5,356,430 of Nadol describes a hearing prosthesis that is deemed to provide relief from hearing loss under certain conditions.

It is thus an object of the invention to provide prolonged relief from conductive hearing loss caused by ailments of the middle ear.

It is another object of the invention to provide a surgical method for ameliorating hearing loss caused by ailments of the middle ear.

SUMMARY OF THE INVENTION

The present invention attains the above and other objects by providing a middle ear prosthesis for treating hearing loss due to ailments of the middle ear. The prosthesis of the invention includes a pliant membrane of biocompatible material formed into a closed synthetic balloon configured to fit in a patient's middle ear. When implanted, the prosthesis at least partially contacts the tympanic membrane. The pliant membrane of the prosthesis is selected to be thin and substantially impermeable to water and to gases during protracted contact with body fluids. The prosthesis includes a reservoir for at least one gas within the closed balloon. The prosthesis has an acoustic impedance that is sufficiently low such that the prosthesis enhances the transfer of sound-induced motions of the tympanic membrane to the ossicles and the inner ear. Hence, the prosthesis of the invention restores tympanic membrane motion so as to enhance transfer of sound through the middle ear to the inner ear of a patient.

According to one aspect of the invention, the prosthetic balloon has an equivalent volume, defined below, that is at least approximately 70% of its physical volume. Selecting the equivalent volume of the balloon to be equal or larger than approximately 70% advantageously results in the balloon having an acoustic impedance that is low enough to effectively couple sound-induced motions of the tympanic membrane to the structures of the middle ear, such as the ossicles and the round window. This in turn enhances transmission of sound to the inner ear of the patient.

According to another aspect of the invention, the prosthesis includes a tab extending from an end of the balloon to provide a handle for manipulating the balloon in order to position it in the middle ear. The tab can include a radioopaque marker for radiographic visualization. In one preferred embodiment of the invention, the prosthetic balloon has an ovaloid shape with a generally elliptical cross section that has a major axis and a minor axis. The ovaloid balloon further has a maximum dimension between a first end and a second end along a principal axis, and with a tab extending outwardly from one of these ends.

In some preferred embodiments of the invention, the biocompatible material for forming the balloon is selected to be a homopolymer or a copolymer containing vinylidene chloride (VDC).

In accord with another aspect of the invention, the balloon contains at least one large-molecule biocompatible gas, e.g., sulfur hexafluoride ($SF_6$). The balloon can also contain at least one naturally occurring atmospheric gas having a partial pressure below its normal partial pressure in the atmosphere. The total pressure of the gas within the synthetic balloon is preferably in a range of approximately 50 mm of $H_2O$ below the atmospheric pressure to approximately 50 mm of $H_2O$ above the atmospheric pressure.

In one preferred embodiment, the invention provides a middle ear prosthesis that includes a gas-filled ovaloid balloon having a length and a width that are adapted for fitting in the middle ear in contact with the tympanic membrane. The balloon is formed of a flexible film, for example a film formed of a polymer of VDC, that is substantially impervious to water and to gases such that the balloon remains inflated after implantation in the middle ear. Accordingly, the balloon maintains a reservoir of gas, thereby allowing transmission of acoustical vibrations. The film is selected to be compliant in order to respond elastically flexibly to acoustical vibrations, thereby transmitting the vibrations through normal or reconstructed ossicles.

In one preferred construction, the balloon is initially filled with a substantial portion, e.g., ten to fifty percent or more, of an unnatural, i.e., non-atmospheric, gas, preferably one to which the balloon wall is substantially impermeable, e.g., $SF_6$. Nitrogen and oxygen are also present, but at lower partial pressures than in the surrounding atmosphere. After implantation of the balloon in the middle ear, the nonatmospheric gas, e.g., $SF_6$, diffuses out of the balloon very slowly over time, and atmospheric gases dissolved in the middle ear fluid, e.g., nitrogen and oxygen, diffuse into the balloon at a rate slightly exceeding the rate of the loss of the non-atmospheric gas. Thus, the balloon, over the course of a few months, spontaneously self-inflates, and stays inflated over an extended time period, i.e., more than one to two years.

Another aspect of the invention relates to disposing a plurality of synthetic balloons in the middle ear, where at least one of the balloons contacts the tympanic membrane. The presence of more than one balloon in the space of the middle ear can advantageously maximize hearing restoration of a patient having an ailment of the middle ear. Each balloon is formed of a thin pliant membrane of biocompatible material that is substantially impermeable to water and to gases during protracted contact with body fluids. Each balloon has a reservoir for at least one gas, and further has an acoustic impedance that is low enough to permit sound-induced motions of the tympanic membrane, the ossicles, and the round window.

Another aspect of the invention provides a surgical method for treating hearing loss of a patient due to ailments of the patient's middle ear. The surgical method includes positioning a closed synthetic balloon, fabricated and structured according to the teachings herein, in the patient's middle ear between the tympanic membrane and the bone covering the cochlea.

Illustrative embodiments of the present invention will be described below relative to the following drawings.

DETAILED DESCRIPTION OF ILLUSTRATED EMBODIMENTS

Figure 1:
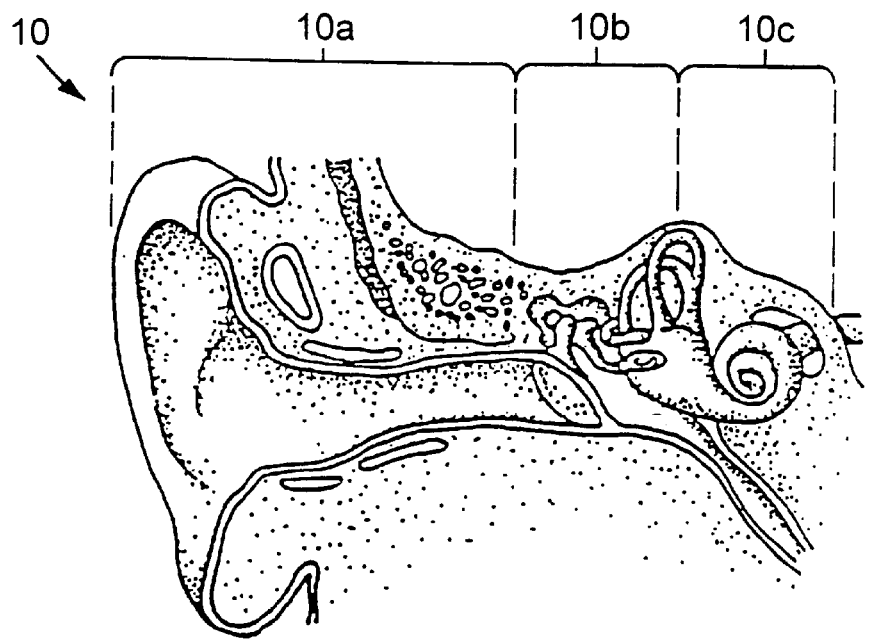
FIG. 1 illustrates schematically the human ear and its operative structures.
Figure 2:
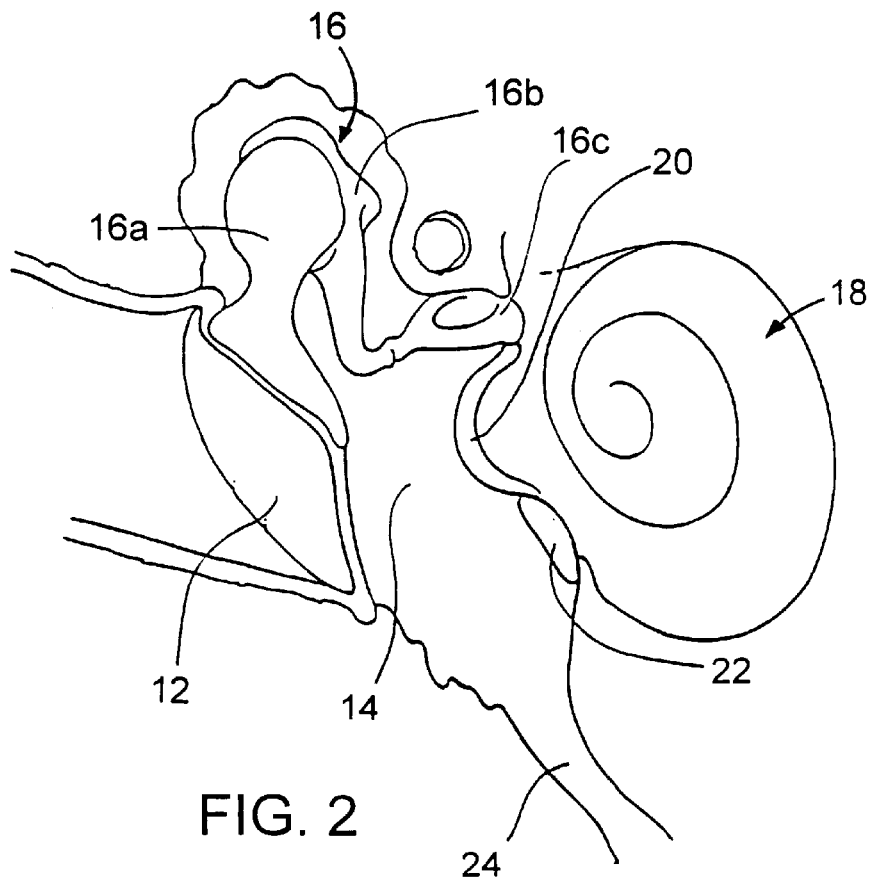
FIG. 2 is an enlarged detail view of the structures of the middle ear.

The present invention provides surgical methods and prosthetic devices for relieving conductive hearing loss caused by ailments of the middle ear. FIGS. 1 and 2 illustrate the human ear 10 and its operative structures by which the auricle, ear canal and drum of the outer ear 10a transmit sound through the middle ear 10b to sensing structures of the inner ear 10c.

FIG. 2 illustrates an enlarged detail view of the structures of the middle ear 10b and their relative sizes and positions. The illustrated structures include the tympanic membrane 12, the middle ear chamber 14, the ossicles 16, the cochlea 18, and the promontory 20. The illustrated structures further include the round window membrane 22, and the eustachian tube 24 that provides air communication with the nasopharynx, thereby equalizing the air pressure in the middle ear chamber 14 with the external atmospheric pressure. The ossicles 16 includes the malleus bone 16a, the incus bone 16b, and the stapes bone 16c.

The middle ear chamber 14, which is ordinarily filled with a gas similar to air maintained at atmospheric pressure via the eustachian tube 24, can become chronically filled with fluid or fibrous tissue, thereby causing a conductive hearing loss. Filling of the middle ear chamber 14 may occur as a result of blockage of the eustachian tube 24 leading to pressure imbalances and other changes that cause fluid to exude from the surrounding tissue. Alternatively, filling of the middle ear chamber 14 may occur as a post-operative tissue deposition, or as a result of infection or inflammatory processes which have a similar effect.

In cases in which the eustachian tube 24 malfunctions, the normal air-filled middle ear chamber 14 can become pathologically altered, resulting in some instances in retraction of the tympanic membrane 12, and inflammatory response in the middle ear, or retention of fluid in the middle ear chamber 14. These conditions can all lead to a conductive hearing loss due to the pathologically induced inefficiency of the sound transmitting system of the middle ear. This is a common finding in chronic active and chronic inactive otitis media (COM), and in otitis media with effusion (OME).

Figure 3:
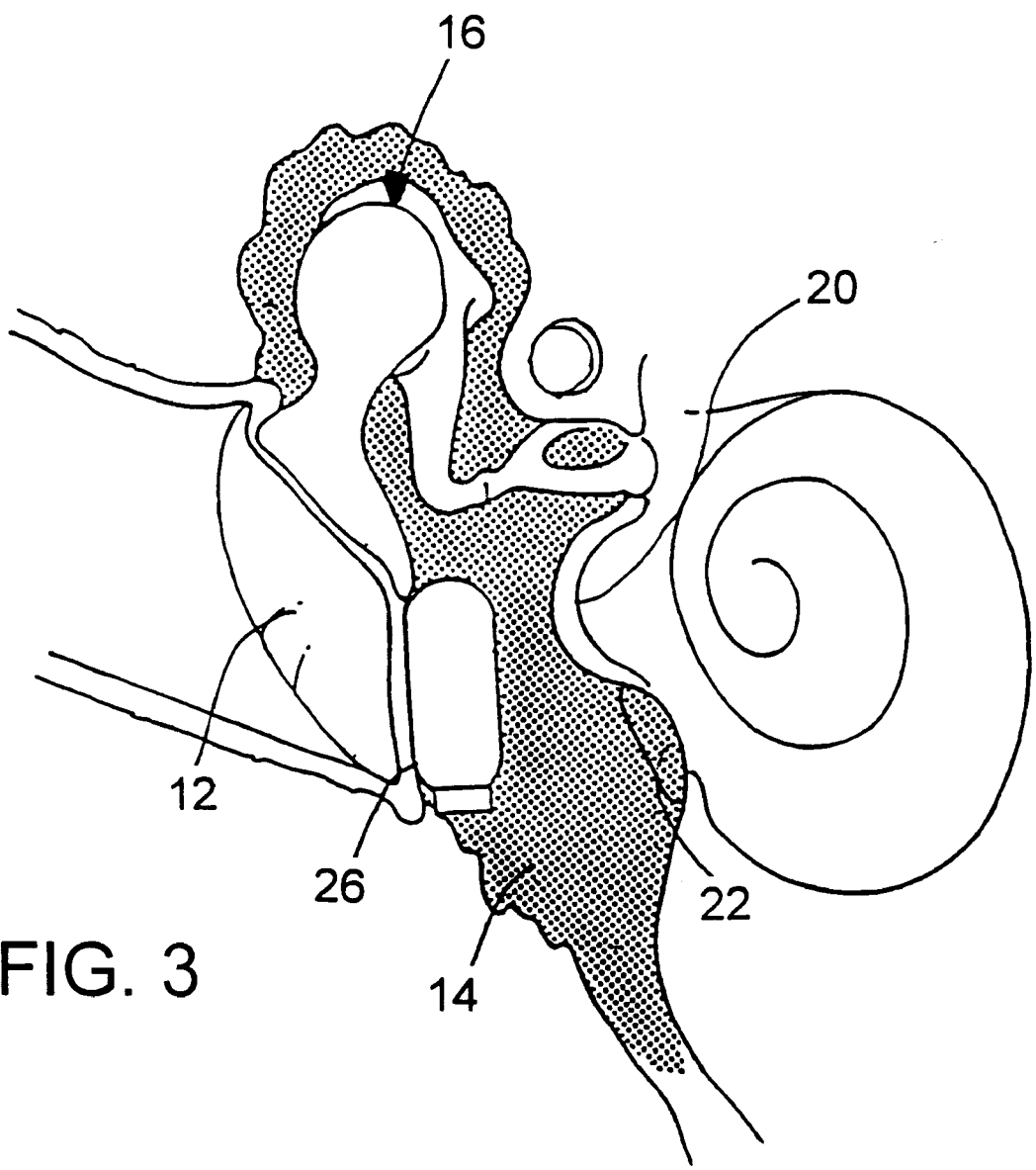
FIG. 3 illustrates one embodiment of a prosthetic device in accordance with the present invention and including a synthetic balloon disposed in the middle ear in contact with the tympanic membrane.

FIG. 3 shows that, in one aspect of the present invention, Applicants surgically implant a middle ear prosthesis in the form of a synthetic balloon 26 in the middle ear chamber 14 of a patient to ameliorate conductive hearing loss. The implanted surgical balloon 26 at least partially contacts the tympanic membrane 12 to allow motion of the tympanic membrane. The implanted synthetic balloon 26 provides a reservoir for gas in a compressible form in the middle ear to effectuate a degree of compliance of the tympanic membrane 12, the ossicles 16, and the round window 22 that is comparable to that of a normal ear. That is, the implantation of the synthetic balloon 26 in the middle ear and in contact with the tympanic membrane 12 enhances movement of the tympanic membrane 12, the ossicies 16, and the round window 22 in response to sound vibrations incident through the external auditory canal on the tympanic membrane 12.

Figure 4A:
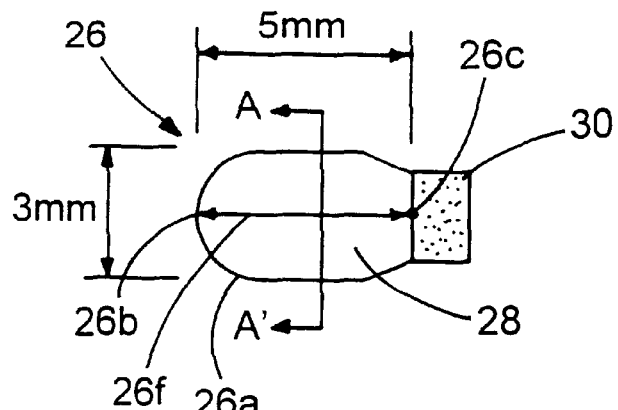
FIG. 4A is a top view of the prosthetic device of FIG. 3.
Figure 4B:
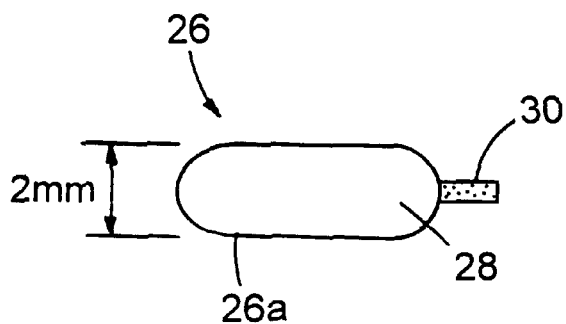
FIG. 4B is a side cross-sectional view of the prosthetic device of FIG. 4A.
Figure 4C:
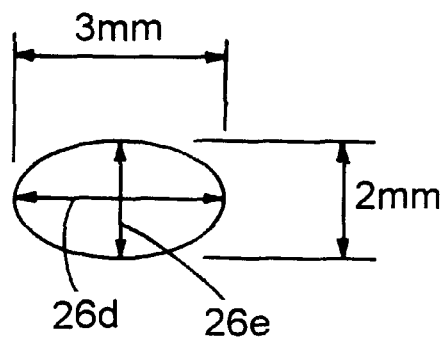
FIG. 4C is a cross-section view, along the line AA', of the prosthetic device of FIG. 4A.

FIGS. 4A, 4B, and 4C show that the synthetic prosthetic balloon 26 has preferably the shape of a jelly bean or a gelatin capsule, the operative form of which is generally convex. The illustrated synthetic balloon 26 includes an ovaloid membrane 26a enclosing a gas-filled volume 28. The prosthetic balloon 26 has a generally elliptical cross-section along the line AA' (FIG. 4C) having a major axis 26d having a length of approximately three millimeters, and a minor axis 26e having a length of approximately two millimeters. Further, the balloon 26 has a principal axis 26f having a length of approximately five millimeters (FIG. 4A) extending from a first end 26b of the balloon 26 to a second end 26c thereof. These dimensions are selected to assure that the prosthetic balloon 26 will fit in the normal middle ear space. A tab 30 extends from the end 26c of the gas-filled volume 28 to provide a handle for surgical manipulation of the balloon 26 in an ear without damaging the balloon wall. The tab 30 preferably contains a filler material, such as barium or iodide, or metallic foil which renders it radioopaque for radiographic visualization.

Applicants have discovered that the synthetic balloon 26 preferably satisfies several primary criteria to attain maximal results for ameliorating conductive hearing loss. In particular, the illustrated synthetic balloon 26 is easily compressible by sound vibrations. That is, the synthetic balloon 26 has a low enough acoustic impedance to permit effective sound induced motions of the tympanic membrane 12, the ossicles 16, and the round window 22, as shown in FIG. 3. Further, the preferred synthetic balloon 26 is non-toxic to the biological environment of the middle ear, i.e., the synthetic balloon 26 is biocompatible. In addition, the synthetic balloon 26 is water impermeable, and has low permeability to gases so that it remains inflated for relatively long periods of time. The balloon 26 also withstands physiological pressure variations of the middle ear. Notwithstanding these several criteria, the prosthesis of the invention can be easily fabricated.

The acoustic impedance of the synthetic balloon 26 can be described in terms of an 'equivalent volume' of the balloon, which is defined as a volume of air whose acoustic impedance equals the acoustic impedance of the balloon at the same ambient pressure and temperature as the balloon. The equivalent volume of the synthetic balloon 26 is determined by the physical volume of air within the balloon, as well as by the elasticity and thickness of the material from which the balloon is formed. The equivalent volume of the balloon 26 is always less than its physical volume, and hence can be expressed as a percentage of its total physical volume.

The synthetic balloon 26 is functionally equivalent to an air bubble having a size equal to the equivalent volume of the balloon 26. As the equivalent volume of a balloon increases, its acoustic impedance decreases, and hence its compressibility increases. Accordingly, an increase in the equivalent volume of the balloon 26 improves its efficacy as a prosthetic device for ameliorating conductive hearing loss. The equivalent volume of the synthetic balloon 26 is preferably selected to be equal or greater than approximately 70% of its physical volume. For example, one preferred practice of the invention selects the elasticity and the thickness of the material forming the balloon 26, which has a volume of approximately thirty microliters as described below, such that the balloon 26 has an equivalent volume that is greater than approximately twenty one microliters. An equivalent volume of twenty one microliters corresponds to an acoustic compliance of $1.5 \times 10^{-13}$ m$^3$/pascal.

Further, a balloon for use in the prosthesis of the invention preferably withstands normal pressure variations in the middle ear without bursting. The effect that pressure variations which occur in a normal middle ear will have on a balloon's shape can be roughly quantified. During commercial airplane travel, the cabin pressure drops to roughly −15.5 cmHg (to 60.8 cmHg absolute). This corresponds to the atmospheric pressure at an altitude of 6000 feet, which covers the maximum altitude of American cities. This reduction in pressure creates a maximum increase of 25% in balloon volume, which corresponds to an increase of less than 8% in diameter. A prosthetic balloon made from a homopolymer or copolymer containing VDC and having a thickness of approximately 0.001 inch to 0.004 inch is deemed able to withstand such a pressure change.

As described above, another criterion for a prosthetic balloon according to this invention is low permeability to gases. In particular, the useful life of the balloon depends upon how long it takes for the gases to permeate out from its interior, thereby causing the balloon to deflate. The criteria of flexibility, i.e., low acoustic impedance, with low permeability for water and gases are competitive, in that thin, soft material is probably best to achieve good acoustic transmission but may have low ability to retard gas permeation.

A preferred embodiment of the balloon 26 employs a film of polyvinylidene chloride (PVDC) (homopolymers and copolymers containing vinylidene chloride (VDC)), as the material for the balloon membrane 26a. VDC polymeric materials are substantially impermeable to air and oxygen, and have excellent water barrier properties. In particular, this embodiment of the invention employs a PVDC film having a thickness of approximately 0.001 inch to produce the synthetic balloon 26. Such a synthetic balloon has a high equivalent volume, i.e., higher than 70%, and thus possesses the required acoustic compressibility characteristics.

One practice of the invention employs film casting to produce a film of PVDC having a thickness in a range of approximately 0.001 inch to approximately 0.004 inch, for construction of the balloon 26. For example, this practice of the invention dissolves granules of a homopolymer of VDC in a non-toxic solvent and spun casts the solution onto glass slides. The concentration of the solution is selected to produce spun cast films having the desired thickness. The cast films are initially dried at room temperature, and subsequently are dried under vacuum to remove residual solvent. This practice of the invention peels off the dried films from the glass substrate to obtain a free-standing film.

A preferred method of manufacturing the prosthetic balloon 26 includes an initial step (1) of draping a PVDC film, having a thickness of approximately 0.001 inch, over a shaping mandrel to create a balloon 'preform' having an open end. Subsequently, in step (2), the preform and the mandrel are inserted into a vacuum cavity that prevents the open end of the perform from closing. In step (3), the shaping mandrel is removed and an air stream is directed through the open end of the balloon preform into its interior space to help maintain a proper balloon shape during a subsequent step of sealing the balloon. In step (4), a side-action heated sealing bar is applied to the preform to close its open end, thereby providing a sealed balloon. In step (5), the sealed balloon is removed from the vacuum cavity and, in step (6), the sealed balloon is trimmed to remove any excess material therefrom, thereby producing a synthetic balloon suitable for use in the present invention. The fabricated balloon has an equivalent volume larger than approximately 80%, and hence has an acoustic impedance that is sufficiently low to allow motions of the tympanic membrane, the ossicles, and the round window, when implanted in the middle ear.

An alternative method for fabricating the synthetic balloon 26 includes solvent casting. Such a method immerses a polished steel mandrel in a solution of PVDC to cast a shell having a thickness in a range of approximately 0.001 to approximately 0.004 inch. Following the casting, the method peels the shell from the mandrel, fills it with gas, and seals it at its open end to form the tab 30 of FIG. 4B.

Referring again to FIG. 3, the implantation of the balloon 26 in the middle ear in contact with the tympanic membrane 12 provides a number of advantages. In particular, the prosthetic synthetic balloon 26 provides an air cushion on the side of tympanic membrane 12 facing the middle ear chamber 14. Such an air cushion advantageously maximizes the motions of the tympanic membrane 12 in response to acoustic waves impinged on the tympanic membrane 12 through the ear canal. Accordingly, the implanted balloon 26 advantageously enhances hearing of patients suffering from middle ear ailments, such as ailments resulting from dysfunction of the eustachian tube. In particular, the implanted balloon 26 enhances hearing of patients with chronic otitis media (COM) and/or otitis media with effusion (OME).

Further, the implanted balloon 26, as a result of its low permeability to gases and to fluids, remains inflated for long periods, and hence advantageously provides long-term relief. In addition, the balloon 26 keeps the tympanic membrane intact, thus obviating the need for water precautions and lessening the risk of repeated infections.

Figure 5:
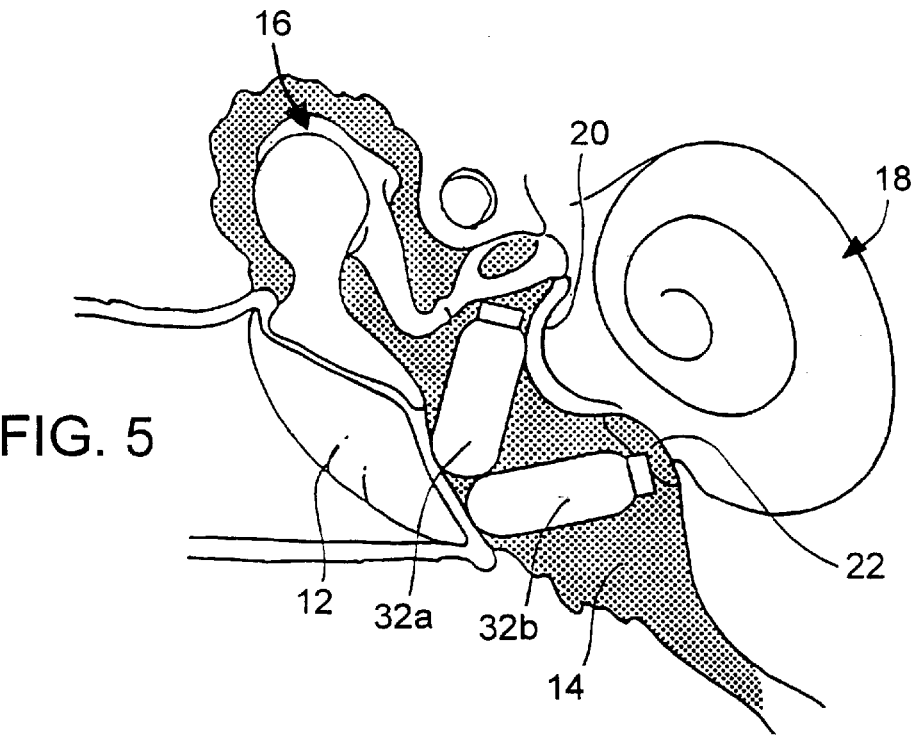
FIG. 5 illustrates two prosthetic balloons, each similar to the prosthetic device of FIG. 3, disposed in the middle ear such that both balloons contact the tympanic membrane.

FIG. 5 illustrates an alternative practice of the present invention, which implants two synthetic balloons 32a and 32b in the middle ear chamber 14. The balloon 32a is disposed in the middle ear chamber 14 between a portion of the tympanic membrane 12 and the promontory 20, and the balloon 32b is disposed in the middle ear chamber 14 between a portion of the tympanic membrane 12 and the round window membrane 22. Hence, each of the synthetic balloons 32a and 32b at least partially contacts the tympanic membrane 12. The presence of two balloons, rather than one, in the middle ear advantageously increases the total equivalent volume of the prosthetic device. In other words, the total acoustic impedance of the two-balloon system of the illustrated balloons 32a and 32b is lower than the individual impedance of each balloon. An increase in the total equivalent volume advantageously improves the efficacy of the prosthetic device for enhancing transmission of sound through the middle ear to the inner ear, thereby ameliorating conductive hearing loss.

Figure 6:
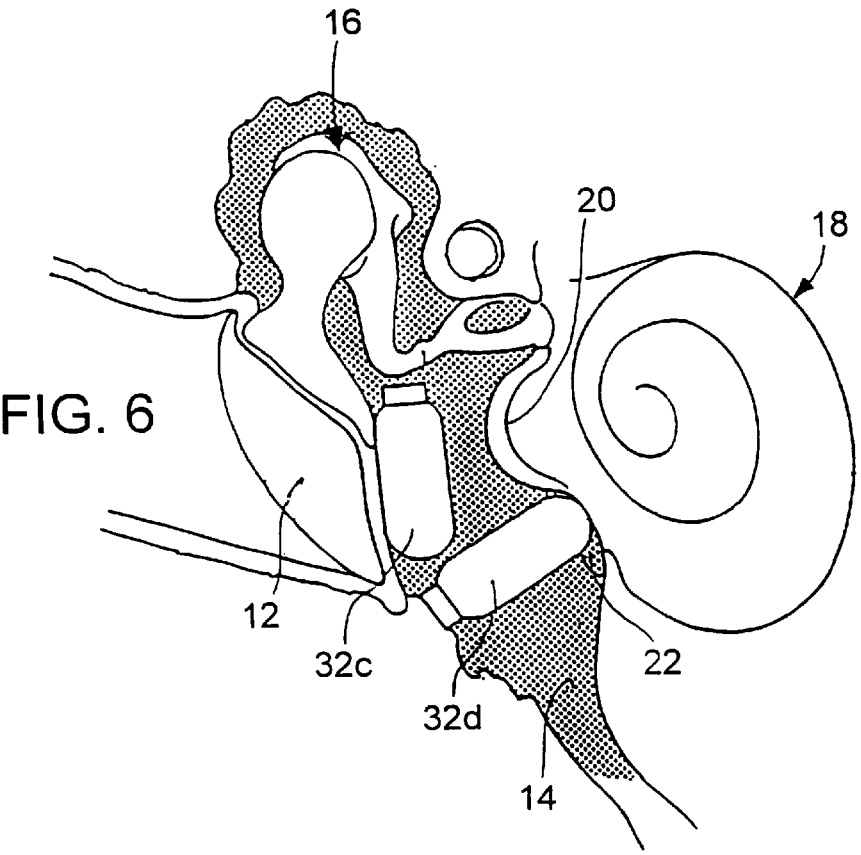
FIG. 6 illustrates the prosthetic balloons of FIG. 5, disposed in the middle ear such that one balloon contacts the tympanic membrane and the other balloon contacts the round window without contacting the tympanic membrane.

FIG. 6 illustrates yet another alternative practice of the invention, which implants two prosthetic balloons 32c and 32d in the middle ear chamber 14. While the balloon 32c contacts the tympanic membrane 12, the balloon 32d is not in contact with the tympanic membrane 12, and is positioned in the middle ear such that it contacts the round window 22.

Those skilled in the art will understand that the number of balloons that can be implanted in the middle ear is not necessarily limited to two. The size of the middle ear space of a patient and the size of the balloons employed typically dictate the maximum number of balloons that can be implanted in the patient's middle ear.

A preferred practice of the invention implants one or more balloons in the middle ear of a patient who suffers from ailments of the middle ear during tympanoplasty surgery. The middle ear is exposed by elevating a tympano-meatal flap, and one or more synthetic balloons are disposed in the middle ear space between the tympanic membrane and the promontory/round window, with at least one balloon contacting the tympanic membrane. The balloons can be positioned between the tympanic membrane and the bone covering the cochlea in the middle ear compartment. The anatomical constraints of the middle ear keep the balloons in stable position. One practice of the implantation of the balloons places absorbable tissue gel material, such as gel-foam or the like, around the implanted balloon to help initially stabilize the balloon in the middle ear space. The placement of the balloons in the middle ear can be combined with repair of the tympanic membrane and/or reconstruction of the ossicles.

While the present invention has been described with reference to above illustrative embodiments, those skilled in the art will appreciate that various changes in form and detail may be made without departing from the intended scope of the present invention as defined in the appended claims.

What is claimed is:

1. A middle ear prosthesis for treating middle-ear hearing loss, said prosthesis comprising
    a pliant membrane of biocompatible material formed into
        a closed synthetic prosthetic balloon configured to fit in a patient's middle ear at least partially in contact with the tympanic membrane, said pliant membrane being thin and substantially impermeable to water and to gases during protracted contact with body fluids, said prosthesis further having a reservoir for at least one gas within said closed balloon and having an acoustic impedance low enough to permit sound-induced motions of the tympanic membrane, ossicles and round window.

2. A middle ear prosthesis according to claim 1, wherein said prosthetic balloon has an equivalent volume of at least approximately 70% of its physical volume.

3. A prosthesis according to claim 1, further comprising a tab extending from an end of said prosthetic balloon to constitute a handle for manipulating said balloon to position it in the middle ear.

4. A prosthesis according to claim 1, wherein said balloon is ovaloid, and has a maximum dimension between a first end and a second end along a principal axis, and a tab extending outwardly from one of said ends.

5. A middle-ear prosthesis according to claim 1, wherein said biocompatible material includes a homopolymer of vinylidene chloride.

6. A middle ear prosthesis according to claim 1, wherein said biocompatible material includes a copolymer containing vinylidene chloride.

7. A middle ear prosthesis according to claim 6, wherein said copolymer further contains methyl acrylate.

8. A middle ear prosthesis according to claim 6, wherein said copolymer further contains acrylonitrile.

9. A middle ear prosthesis according to claim 6, wherein said copolymer further contains vinyl chloride.

10. A prosthesis according to claim 1, wherein said gas comprises at least one large molecule biocompatible gas.

11. A prosthesis according to claim 10, wherein said one large molecule is sulfur hexafluoride.

12. A prosthesis according to claim 1, wherein said balloon fits loosely in the middle ear and wherein said gas comprises at least one naturally occurring atmospheric gas, said naturally occurring gas having a partial pressure within said reservoir below a normal partial pressure of said gas in the atmosphere.

13. A prosthesis according to claim 3, wherein said tab includes a radioopaque marker.

14. A middle ear prosthesis, said prosthesis comprising a gas-filled ovaloid balloon having a width adapted for fitting in the middle ear at least partially in contact with the tympanic membrane and having a length no greater than a height of the middle ear cavity, said balloon being formed of a flexible film which is substantially impervious to water and to gases such that said balloon remains inflated after implanting to maintain a reservoir of gas, said film being compliant for deforming flexibly responsive to acoustical vibrations for transmitting said vibrations through the tympanic membrane and through normal or reconstructed ossicles to the inner ear.

15. A middle-ear prosthesis according to claim 14, wherein said flexible film includes a homopolymer of VDC.

16. A middle-ear prosthesis according to claim 14, wherein said flexible film includes a copolymer containing VDC.

17. A middle ear prosthesis according to claim 14, wherein said ovaloid balloon has a longitudinal major axis and minor transverse axes, and further comprising a tab extending from an end of the balloon along said major axis.

18. A middle ear prosthesis according to claim 14, wherein said gas comprises air.

19. A middle ear prosthesis according to claim 14, wherein said balloon gas comprises at least a large-molecule gas and air.

20. A middle ear prosthesis according to claim 19, wherein said large-molecule gas is sulfur hexafluoride.

21. A middle ear prosthesis according to claim 14, wherein said balloon has means for self-inflating including a film and air at sub atmospheric pressure effective for self inflation by diffusion after implanting.

22. A middle ear prosthesis according to claim 14, wherein said reservoir of gas contains air at sub-atmospheric pressure.

23. A middle ear prosthesis according to claim 14, further comprising means for initiating self-inflation including gases at partial pressure effective to initiate self-inflation.

24. A middle ear prosthesis according to claim 14, wherein said balloon has a convex closed surface for smoothly contacting surrounding tissue.

25. An apparatus for treating hearing loss due to an ailment of the middle ear, said apparatus comprising
a plurality of prosthetic closed synthetic balloons configured to fit in a patient's middle-ear with at least one of said balloons being formed of a thin pliant membrane of biocompatible material that is substantially impermeable to water and to gases during protracted contact with body fluids, each of said balloons having a reservoir for at least one gas and having an impedance low enough to permit sound-induced motions of the tympanic membrane, ossicles and round window.

26. A surgical method for treating middle-ear hearing loss of a patient, said method comprising the step of
positioning a closed synthetic prosthetic balloon, having a reservoir for at least one gas, in the patient's middle ear at least partially in contact with the tympanic membrane, said synthetic balloon being formed of a thin pliant membrane of biocompatible material such that said balloon has an impedance low enough to permit sound-induced motions of the tympanic membrane, ossicies and the round window, said pliant membrane being substantially impermeable to water and to gases during protracted contact with body fluids.

27. A surgical method according to claim 26, wherein the step of positioning a closed synthetic balloon includes positioning the balloon between the tympanic membrane and the bone covering the cochlea.

28. A surgical method according to claim 27, further comprising the step of exposing the patient's middle ear by elevating a tympano-meatal flap before disposing said synthetic balloon in the middle ear.

* * * * *